(12) United States Patent
Cronin et al.

(10) Patent No.: US 6,930,773 B2
(45) Date of Patent: Aug. 16, 2005

(54) SPECTRAL IMAGING

(75) Inventors: Paul J. Cronin, Charlestown, MA (US); Peter J. Miller, Newburyport, MA (US)

(73) Assignee: Cambridge Research and Instrumentation, Inc., Woburn, MA (US)

( * ) Notice: Subject to any disclaimer, the term of this patent is extended or adjusted under 35 U.S.C. 154(b) by 273 days.

(21) Appl. No.: 10/226,592

(22) Filed: Aug. 23, 2002

(65) Prior Publication Data

US 2003/0081204 A1 May 1, 2003

Related U.S. Application Data

(60) Provisional application No. 60/314,367, filed on Aug. 23, 2001.

(51) Int. Cl.$^7$ .................................................. G01J 3/00
(52) U.S. Cl. ..................... 356/300; 356/320; 250/339.12
(58) Field of Search ................................ 356/320, 317, 356/318; 250/339.12, 339.01; 702/23; 700/226

(56) References Cited

U.S. PATENT DOCUMENTS

| | | |
|---|---|---|
| 4,379,233 A | 4/1983 | Rosenthal |
| 4,519,707 A | 5/1985 | Kuffer |
| 4,669,878 A | 6/1987 | Meier |
| 4,800,279 A | 1/1989 | Hieftji et al. |
| 5,029,245 A | 7/1991 | Keranen et al. |
| 5,042,893 A | 8/1991 | Ong |
| 5,066,124 A | 11/1991 | Wulf |
| 5,137,364 A | 8/1992 | McCarthy |
| 5,424,545 A | 6/1995 | Block et al. |
| 5,433,197 A | 7/1995 | Stark |
| 5,435,309 A * | 7/1995 | Thomas et al. ............. 600/310 |
| 5,539,517 A | 7/1996 | Cabib et al. |
| 5,567,937 A | 10/1996 | Pinkus |
| 5,608,213 A | 3/1997 | Pinkus et al. |
| 5,719,024 A | 2/1998 | Cabib et al. |
| 5,731,581 A * | 3/1998 | Fischer et al. ......... 250/339.13 |
| 5,732,150 A | 3/1998 | Zhou et al. |
| 5,760,407 A | 6/1998 | Margosiak et al. |
| 5,838,451 A | 11/1998 | McCarthy |
| 5,857,462 A | 1/1999 | Thomas et al. |
| 6,035,246 A | 3/2000 | Wagner |
| 6,075,595 A | 6/2000 | Malinen |
| 6,142,629 A | 11/2000 | Adel et al. |
| 6,160,618 A | 12/2000 | Garner |
| 6,341,257 B1 | 1/2002 | Haaland |
| 6,373,568 B1 | 4/2002 | Miller et al. |

FOREIGN PATENT DOCUMENTS

WO    WO 01/11343    2/2001

* cited by examiner

*Primary Examiner*—Layla G. Lauchman
(74) *Attorney, Agent, or Firm*—Fish & Richardson P.C.

(57) ABSTRACT

A method is described that includes measuring, at each of a set of W wavelength bins, a spectral response of at least one region of a sample stained with multiple stains, and determining the concentration of at least one of the stains in the region of the sample based in part on the spectral responses, the wavelength bins being chosen so that a matrix of elements that represent the responses of the stains at the wavelength bin has an inverse for which a mathematical stability is maximum relative to the inverses of other matrices of elements that represent the responses of the stains for other possible sets of wavelength bins.

44 Claims, 3 Drawing Sheets

SPECTRAL IMAGING

CROSS-REFERENCE TO RELATED APPLICATIONS

This application claims priority from U.S. provisional patent application Ser. No. 60/314,367 entitled "Multispectral Imaging Method and Apparatus" by Paul J. Cronin and Peter J. Miller, filed Aug. 23, 2001. The contents of the provisional application are incorporated herein by reference.

BACKGROUND

Researchers have long characterized samples, such as biological tissue samples, by measuring spectral response. Staining techniques deposit stains in specific locations and spatial images of the sample can often identify the spatial location of the stains and their staining targets. For example, methods such as histochemistry, immunohistochemistry, and in-situ hybridization specifically target macromolecules, nucleic acid sequences or specific antigens. After binding to such targets, these techniques deposit stains in the vicinity of the targets. In many applications, multiple staining protocols are used simultaneously and measuring the concentration of each stain in the sample provides highly relevant multiplexed data about the sample.

Often the stains overlap and the resulting spectral response of the sample represents the overlapping spectral responses of the mixture of the stains. Quantifying the separate concentrations of these coexistent stains is known as spectral unmixing. In some cases spectral unmixing can be challenging. For example, in transmission spectroscopy Beer's law governs the relation between stain concentration and transmitted light intensity and as this relation is exponential it can prove to be challenging to linear unmixing methods.

Typical spectral unmixing methods acquire an entire image cube of the sample.

Intensity data is recorded for each 2D spatial pixel at each of a number of wavelengths. Using this data, the methods determine the multiple stain concentrations present in the sample. Typically such methods collect large amounts of data for each sample and use a spectral imaging system capable of measuring sample response at each of the different wavelengths.

SUMMARY

In general, in one aspect, the invention features a method including: (i) measuring the intensity of a spectral response of at least one region of a sample stained with N multiple stains to each of K spectra $A_k$, wherein the K spectra collectively include energy at W wavelength bins and wherein $K \geq N$; and (ii) determining the concentration of at least one of the stains in the region of the sample based in part on the spectral responses. The W wavelength bins are selected such that the matrix of elements that represent the response of each of the N stains at each of the W wavelength bins has an inverse for which a mathematical stability is maximum relative to the inverses of other matrices of elements that represent the responses of the stains for other possible sets of wavelength bins.

Embodiments of the method may include any of the following features.

The method may further include determining the concentration of all of the multiple stains in the region of the sample based in part on the spectral responses.

Each of the spectra $A_k$ may have energy at only one of the W wavelength bins.

W may equal K. W may equal N. Moreover, W may equal N and K.

For embodiments in which W=K, the mathematical stability of the inverse of the matrix of elements S may be calculated according to $$\frac{\det[S]}{\sum_{i=1}^{K} \sum_{j=1}^{W} (S_{i,j})^2}.$$

Determining the concentration of the at least one stain may include an optical density conversion.

The spectral response of the sample may include an absorption response.

The spectral response of the sample may include a fluorescence response.

The sample may includes an optically thin sample.

Measuring the intensity of the spectral response for each spectra $A_k$ may include: illuminating the region of the sample with radiation corresponding to each of the K spectra $A_k$, and measuring the intensity of radiation emerging from the region of the sample in response to the illumination with each spectra $A_k$.

Alternatively, measuring the intensity of the spectral response for each spectra $A_k$ may include: illuminating the region of the sample with broadband radiation, filtering the radiation emerging from the region of the sample in response to the broadband illumination with a filter corresponding to each of the K spectra $A_k$, and measuring the intensity of the filtered radiation for each of the K spectra $A_k$.

The method may further include selecting the W wavelength bins based at least in part on the mathematical stability of the inverse of the matrix of elements that represent the response of each of the N stains at each of the W wavelength bins.

In general, in another aspect, the invention features a method including: (i) obtaining a spectral response for each of P stains; and (ii) selecting a set of W wavelength bins such that a matrix of elements that represent the responses of N of the P stains at the W wavelength bins has an inverse for which a mathematical stability is maximum relative to the inverses of other matrices of elements that represent the responses of the stains for other possible sets of wavelength bins and choices of N stains.

Embodiments of the method may include any of the following features.

P may equal N. Alternatively, P may be greater than N. Furthermore, W may equal N.

The spectral response of the sample may include an absorption response.

The spectral response of the sample may include a fluorescence response.

The method may further include instructing a spectral imaging apparatus to measure the spectral response of a sample stained with the N stains to measure the spectral response at the set of wavelength bins.

For embodiments in which W=N, the mathematical stability of the inverse of the matrix of elements S may be calculated according to $$\frac{\det[S]}{\sum_{i=1}^{N}\sum_{j=1}^{W}(S_{i,j})^2}.$$

In general, in another aspect, the invention features a method including: (i) obtaining a spectral response for each of P stains; (ii) determining, for each of multiple sets of W wavelength bins, the mathematical stability of an inverse of a matrix of elements that represent the responses of N of the P stains to the corresponding set of W wavelength bins; and (iii) selecting one of the multiple sets of W wavelength bins based at least in part on the magnitude of its mathematical stability relative to those of the other sets of wavelength bins.

Embodiments of the method may include any of the following features.

P may equal N. Alternatively, P may be greater than N. Furthermore, W may equal N.

For embodiments in which W=N, the mathematical stability of the inverse of the matrix of elements S may be calculated according to $$\frac{\det[S]}{\sum_{i=1}^{N}\sum_{j=1}^{W}(S_{i,j})^2}.$$

The method may further include: measuring the intensity of a spectral response of at least one region of a sample stained with the N stains to each of K spectra $A_k$, wherein the K spectra collectively include energy at the W wavelength bins and wherein K≧N; and determining the concentration of at least one of the stains in the region of the sample based in part on the spectral responses of the sample.

Embodiments of the method that include these measuring and determining steps may further include any of the following features.

The method may further include determining the concentration of all of the multiple stains in the region of the sample based in part on the spectral responses.

Each of the spectra $A_k$ may have energy at only one of the W wavelength bins.

W may equal K. W may equal N. Moreover, W may equal N and K.

Determining the concentration of the at least one stain may include an optical density conversion.

The spectral response of the sample may include an absorption response.

The spectral response of the sample may include a fluorescence response.

The sample may includes an optically thin sample.

Measuring the intensity of the spectral response for each spectra $A_k$ may include: illuminating the region of the sample with radiation corresponding to each of the K spectra $A_k$, and measuring the intensity of radiation emerging from the region of the sample in response to the illumination with each spectra $A_k$.

Alternatively, measuring the intensity of the spectral response for each spectra $A_k$ may include: illuminating the region of the sample with broadband radiation, filtering the radiation emerging from the region of the sample in response to the broadband illumination with a filter corresponding to each of the K spectra $A_k$, and measuring the intensity of the filtered radiation for each of the K spectra $A_k$.

In general, in another aspect, the invention features a method including: based on spectral responses of N stains, selecting N wavelength bins for measurement of samples containing the N stains, the N wavelength bins being selected to minimize errors in stain concentration computed from the measurements of the samples.

In general, in another aspect, the invention features an apparatus including a spectral illuminator to emit light in W wavelength bins, with the intensity of light in each spectral band being independently adjustable, and to measure a spectral response of the sample stained with N stains, and wherein a matrix of elements that represent the responses of N the stains at the W wavelength bins has an inverse for which a mathematical stability is maximum relative to the inverses of other matrices of elements that represent the responses of the N stains for other possible sets of wavelength bins.

Embodiments of the apparatus may include any of the following features.

W may equal N. The spectral response of the sample may include an absorption response. The spectral response of the sample may includes a fluorescence response.

For embodiments in which W=N, the mathematical stability of the inverse of the matrix of elements S may be calculated according to $$\frac{\det[S]}{\sum_{i=1}^{N}\sum_{j=1}^{W}(S_{i,j})^2}.$$

Among the advantages of the invention are one or more of the following. A number of exposures necessary for spectrally unmixing N stains is minimized. For a set number of exposures and a given set of stains, choosing the optimum set of wavelength bins at which to measure the spectral response optimizes the precision of the stain concentration computation. Such selection is of great benefit since it requires neither an expert knowledge of spectral analysis, nor of the samples to be analyzed, and thus can be used to automate the selection of wavelengths for observation and analysis, which is otherwise a burdensome, subjective, and delicate task. Further, the time required for spectrally unmixing N stains may be optimized. Cheaper and simpler spectral imaging systems may be used.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
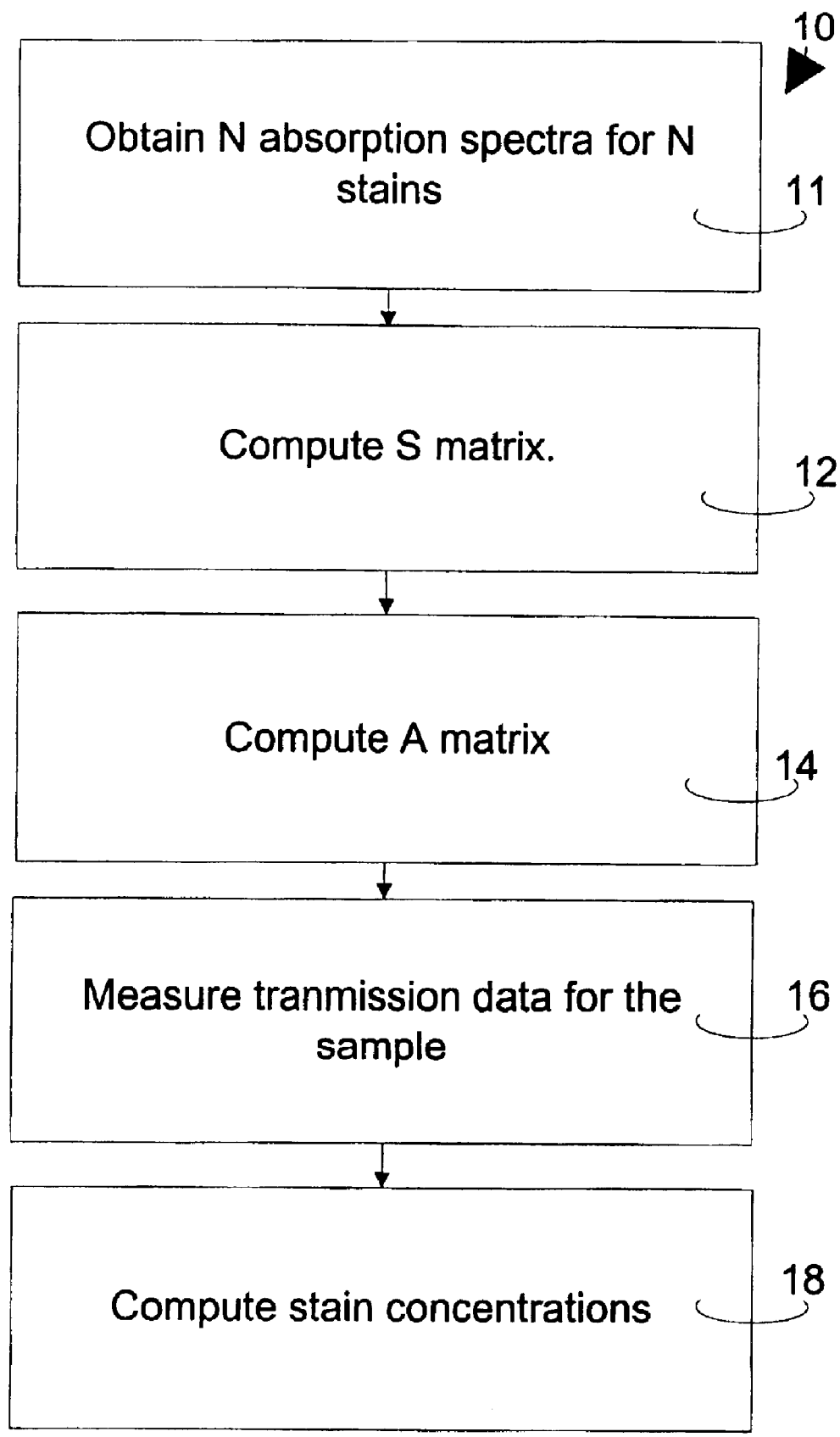
FIG. 1 is a flow diagram of a method for computing the concentrations of N stains in a sample.

Quantifying the concentration of N stains requires a minimum of only N measures of the spectral response of a sample at a minimum of only N wavelength bins. The choice of wavelength bins influences the precision of the stain concentration computation. Notably, the N wavelengths may be chosen based on the features of the spectral response of the N stains so as to minimize the errors in the computed stain concentrations.

Some embodiments may implement algorithms that reduce the number of images recorded for quantitative results, thereby maximizing the throughput of multispectral imaging test stations. Although the description below uses the generic term stain, the applicability of that term extends to any protocol for preferentially depositing a substance that interacts with light in a sample at specific locations.

Many embodiments involve the transmission of light through an absorbing media. Under such conditions, the light intensity is reduced in an exponential manner. However, a transform to optical density allows for a linear unmixing. With an optical density conversion the process becomes linear and the unmixing procedure accurately separates the multiple stains.

In what follows, a general model is presented for quantitatively determining the concentrations of absorbing stains at each location across the plane of the sample. For this purpose, a set of 2D images of the specimen is acquired. In some embodiments, the smallest set of images needed to compute the concentrations of all of the absorbing stains at all locations is acquired. We show that the number of stains in that smallest set is the same as the number of stains. The method then uses the set of images to quantify the 2D distribution of all of the absorbing stains throughout the specimen. When using the minimum number of images, the method repeatedly measures the sample with a different single wavelength bin belonging to an optimal set of wavelength bins. Once this optimal set of wavelength bins is found, they may be broadly used since they relate not to a particular specimen, but of the optical properties of the set of stains themselves.

Implementations are also discussed for an optically thin specimen. For example, an optically thin sample can be one that is physically very thin or has a very low concentration of absorbing agents. The analysis used for the special case is easily modified for use with fluorescent samples, rather than samples with absorbing agents. In these cases, the method does not use an 'optical density' conversion (described later) to determine the quantities of the stains.

The description that follows discusses the analysis for one pixel of a charge-coupled device (CCD) that collects the images of the sample. Similar processing is typically done for all pixels of the CCD to provide spatially extended images.

Consider a monochromatic ray with wavelength $\lambda$ impinging a specimen that bears an absorbing stain. The fraction of light transmitted through the stain depends upon $S(\lambda)$ the stain's attenuation coefficient at that wavelength and c, the local concentration of the stain. Beer's law relates the transmitted light intensity to the concentration of the absorber according to the following relationship $$B(\lambda) = A(\lambda) exp[-S(\lambda)c] \quad [1]$$

where $B(\lambda)$ is the measured intensity at the CCD for a particular measurement wavelength $\lambda$, and $A(\lambda)$ is the measured intensity without the specimen in the optical path. However there may be multiple stains overlapping within the 2D image area of one pixel. With N stains in a sample, Eq. [1] is expanded to allow for the extra stains as follows $$B(\lambda) = A(\lambda) exp[-S_1(\lambda)c_1] exp[-S_2(\lambda)c_2]\ldots exp[-S_N(\lambda)c_N] \quad [2]$$

$$= A(\lambda) exp\left[-\sum_{i=1}^{N} S_i(\lambda)c_i\right]$$

where $S_i(\lambda)$ and $c_i$ are respectively the absorption coefficient spectra and concentration for the $i^{th}$ stain. If there are no stains at a point, $c_i$ will be zero for all i and no absorption will occur.

Figure 3:
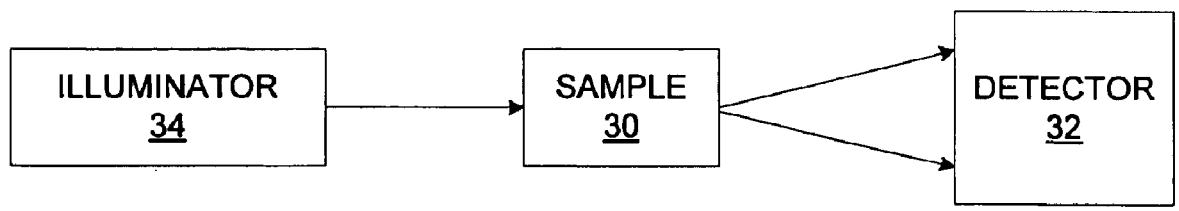
FIG. 3 is an apparatus for illuminating and measuring a spectral response from a sample.

If the specimen is measured using a spectrum of light containing W different wavelengths instead of only a single wavelength, the total detected energy can be derived from Eq. [2] as follows $$B = \sum_{j=1}^{W} A_j exp\left[-\sum_{i=1}^{N} S_{j,i}c_i\right] \quad [3]$$

where $S_{ji}$ is the absorption coefficient for the ith stain at the jth wavelength and $A_j$ is the intensity of the jth measurement wavelength. Note that the intensity levels add as this is an incoherent measurement system. If the sample 30 (FIG. 3) is measured in series with K different measurement spectra, each with W wavelengths with intensities $A_{kj}$, then the energy at the detector 32 (FIG. 3) for the kth measurement spectrum is given by $$B_k = \sum_{j=1}^{W} A_{k,j} exp\left[-\sum_{i=1}^{N} S_{j,i}c_i\right] \quad [4]$$

where $A_{kj}$ is the intensity of the jth wavelength within the kth measurement spectrum. Assuming K measurement spectra, we can rewrite Eq. [4] in matrix form to give $$\begin{bmatrix} B_1 \\ B_2 \\ \vdots \\ B_{K-1} \\ B_K \end{bmatrix} = \begin{bmatrix} A_{1,1} & A_{1,2} & \cdots & A_{1,W-1} & A_{1,W} \\ A_{2,1} & A_{2,2} & & & \vdots \\ \vdots & & \ddots & & \vdots \\ A_{K-1,1} & & & \ddots & \vdots \\ A_{K,1} & \cdots & \cdots & \cdots & A_{K,W} \end{bmatrix} \cdot \begin{bmatrix} exp\left[-\sum_{i=1}^{N} S_{1,i}c_i\right] \\ \vdots \\ exp\left[-\sum_{i=1}^{N} S_{W,i}c_i\right] \end{bmatrix} \quad [5]$$

Given the above outline describing the dependence of transmitted light intensity B and stain concentrations c, the discussion turns to describe a method that quantifies the concentration of N stains. Such a method is outlined in method 10 shown in FIG. 1. Referring to FIG. 1, the method first obtains the N absorption spectra for the N stains (Step 11). By analyzing the absorption spectra, the method computes the W×N matrix S (Step 12). The elements of the S matrix, $S_{ji}$ are the absorption coefficients for the ith stain at the jth wavelength bin. Method 10 computes the set of W wavelength bins at which to measure the spectral response of the sample that optimizes the stability of the computation. Then the method computes the optimum K measurement spectra with which to measure the sample. These K spectra form the K×W matrix A where $A_{kj}$, is the intensity of the jth wavelength bin within the kth measurement spectrum (Step 14). Using the measurement spectral distribution as defined in matrix A, the method measures the K intensity images (Step 16); that is, intensity images are captured for the K different measurement spectra. Using the K intensity images, the method computes the stain concentrations (Step 18). Details of the different steps are described further below.

To obtain a spectral response from a sample corresponding to a particular measurement spectra $A_k$, the sample may be illuminated with excitation radiation corresponding to the particular measurement spectra. For example, the multispectral imaging apparatus described in the commonly-owned U.S. Pat. No. 6,373,568 by Peter J. Miller et al. entitled "Spectral Imaging System" filed Aug. 7, 2000, the contents of which are incorporated herein by reference, discloses a multispectral illuminator 34 (FIG. 3) that produces excitation radiation have adjustable intensities in each of multiple spectral bands. Alternatively, in other embodiments, the sample may be illuminated with broadband radiation (e.g., white light), and the light emerging from the sample in response to the broadband radiation can then be spectrally filtered according to the particular measurement spectra (subject to any compensation for nonuniformity in the broadband illumination radiation). The intensity of the spectrally filtered light then corresponds to the spectral response for that particular measurement spectra. One suitable filter for this purpose is the VARISPEC™ tunable liquid crystal filter available commercially from Cambridge Research and Instrumentation (Woburn, Mass.). In either case, whether the measurement spectra are applied to the illumination of the sample (e.g., by using a spectral imaging system with a multispectral illuminator) or to the emission from the sample (e.g., by using a spectral imaging system with a tunable spectral filter), the algorithms described above and below may be incorporated directly into the electronic processing components of the multi-spectral imaging apparatus, or could be provided separately.

In order to better understand the details of method 10, it is helpful to begin first with a discussion of the last step of method 10 (Step 18). In order to compute the stain concentrations, method 10 inverts Eq. [5] and derives the N stain concentrations c, from the K intensity images $B_1$ to $B_K$. Computing the matrix inverse of A gives $$\begin{bmatrix} \exp\left[-\sum_{i=1}^{N} S_{1,i} c_i\right] \\ \vdots \\ \exp\left[-\sum_{i=1}^{N} S_{W,i} c_i\right] \end{bmatrix} = \begin{bmatrix} A_{1,1} & A_{1,2} & \cdots & A_{1,W-1} & A_{1,W} \\ A_{2,1} & A_{2,2} & & & \vdots \\ \vdots & & \ddots & & \vdots \\ A_{K-1,1} & & & \ddots & \vdots \\ A_{K,1} & \cdots & \cdots & \cdots & A_{K,W} \end{bmatrix}^{-1} \begin{bmatrix} B_1 \\ B_2 \\ \vdots \\ B_{K-1} \\ B_K \end{bmatrix} \equiv \begin{bmatrix} D_1 \\ D_2 \\ \vdots \\ D_{K-1} \\ D_K \end{bmatrix} \quad [6]$$

Taking the natural logarithm of both sides of Eq. [6] and by rewriting the left hand side of Eq. [6] in matrix form yields $$\begin{bmatrix} -\sum_{i=1}^{N} s_{i,1} c_i \\ \vdots \\ -\sum_{i=1}^{N} s_{i,W} c_i \end{bmatrix} = -\begin{bmatrix} S_{1,1} & S_{1,2} & \cdots & S_{1,N-1} & S_{1,N} \\ S_{2,1} & S_{2,2} & & & \vdots \\ \vdots & & \ddots & & \vdots \\ S_{W-1,1} & & & \ddots & \vdots \\ S_{W,1} & \cdots & \cdots & \cdots & S_{W,N} \end{bmatrix} \begin{bmatrix} c_1 \\ c_2 \\ \vdots \\ c_{N-1} \\ c_N \end{bmatrix} = \begin{bmatrix} \ln[D_1] \\ \ln[D_2] \\ \vdots \\ \ln[D_{K-1}] \\ \ln[D_K] \end{bmatrix}. \quad [7]$$

This last step, taking the natural logarithm of $D_1$, is often referred to as a conversion to optical density.

By computing the inverse of S, the stain concentrations are given by:

$$\begin{bmatrix} c_1 \\ c_2 \\ \vdots \\ c_{N-1} \\ c_N \end{bmatrix} = -\begin{bmatrix} S_{1,1} & S_{1,2} & \cdots & S_{1,N-1} & S_{1,N} \\ S_{2,1} & S_{2,2} & & & \vdots \\ \vdots & & \ddots & & \vdots \\ S_{W-1,1} & & & \ddots & \vdots \\ S_{W,1} & \cdots & \cdots & \cdots & S_{W,N} \end{bmatrix}^{-1} \begin{bmatrix} \ln[D_1] \\ \ln[D_2] \\ \vdots \\ \ln[D_{K-1}] \\ \ln[D_K] \end{bmatrix}. \quad [8]$$

Using Eq. [6] and [8], the method computes the stain concentrations based on $B_K$, $S^{-1}$, and $A^{-1}$. In order for the inverses to exist, mathematical validity requires that the number of equations must be equal or greater than the number of unknowns, which can be written as $K \geq W$ and $W \geq N$. In addition to Eqs. [5] and [7] being invertible, method computes the concentrations in Eq. [6] and [8] by choosing matrices A and S such that the resulting concentrations have the smallest error for a given number of exposures K. In some embodiments, method 10 uses the minimum number of exposures K to solve for the concentrations. In such embodiments, K=W=N and the following discussion provides details about such an embodiment. In some embodiments, A or S is not a square matrix (ie K>W or W>N) and the method employs a least square error approach to solve Eqs. [5] or [7]. For example, some embodiments use Singular Value Decomposition (SVD). Such embodiments are discussed later.

In embodiments with K=W=N, the resulting matrices A and S are inverted using well-known techniques for computing inverses of square matrices. Furthermore, as described above, the matrices A and S are chosen so as to minimize the errors in the resulting inverses $S^{-1}$ and $A^{-1}$.

In such embodiments, method 10 begins by obtaining the N absorption spectra for the N stains in the sample (Step 11). In some embodiments, the spectra are obtained from reference sources such as spectral encyclopedias. In other embodiments, the spectra are obtained by taking samples of the stains and directly measuring the absorption spectra with a suitable spectral imaging apparatus. The spectra are measured over a bandwidth, A, typically defined as the bandwidth of a spectral imaging system that later images the sample. Furthermore, the absorption spectra are typically measured with a resolution that is equal to or greater than the resolution δ of the spectral imaging system.

Having obtained the N absorption spectra, the method chooses the optimum S matrix. The S matrix is chosen to have an inverse, $S^{-1}$, with optimized stability. A number of different measures are available to determine the stability of an inverse, as is discussed in texts on linear mathematics. For example, one measure of stability of the inverse matrix is known as the Schwarz measure, which is applicable to square matrices and is given by:

$$\text{stability of inverse} \propto \frac{\det[S]}{\sum_{i=1}^{K} \sum_{j=1}^{W} (S_{i,j})^2}. \quad [9]$$

where det[ ] is the determinant of a matrix. Although the values of the absorption spectra are fixed, method 10 chooses the wavelength bins at which to measure the spectral response. For example, if the absorption spectra span a bandwidth A with a resolution δ, then the absorption spectra are divided into M≡A/δ wavelength bins from which to choose. Method 10 chooses a set of W wavelength bins from the M candidates that optimizes the stability of the inverse of matrix S as defined by Eq. [9]. In this description, the term wavelength bin is used to describe a range of wavelengths. In the example described above the bandwidth Δ is divided evenly into M wavelength ranges of width δ. Although such a division is quite natural, other embodiments divide the bandwidth Δ in other ways using nonuniform spacings and even overlapping ranges for the bins. This division of the bandwidth may be driven by practical considerations or theoretical factors. One practical reason is that, when using a tunable filter to acquire the images, the spectral bandwidth is not uniform with wavelength, but increases at longer wavelengths. Such a filter inherently samples wavelength bins of various widths, and one may choose to center the bins using a grid that, similarly, increases the spacing at longer wavelengths; for example, one might choose the step between wavelengths to be a fixed multiple of the bandwidth at that wavelength. Another practical reason would be for an apparatus that exhibits spectral limitations that bar use of certain wavelength bands. Dichroic filter sets such as are commonly used in epi-illumination microscopes pose such a limitation, in that only certain portions of the spectrum are available for study.

One may also have an a priori basis for eliminating certain spectral ranges, or for sampling a portion of the spectral range more densely than others. If one is using stains that all exhibit little spectral structure in a given spectral region, one may elect not to sample that region at all; conversely, a spectral region in which the stains exhibit dense structure may be more densely sampled. The techniques that we describe can accommodate the use of unevenly spaced bins, and bins of unequal widths, whether undertaken for the exemplary reasons listed above, or for any other reason.

The method finds an optimum choice of wavelength bins by trying each possible S matrix and by evaluating its stability. The total number of matrices to be tested is given by $$^M C_N = \frac{m!}{(m-n)! n!} \quad [10]$$

For example, given N=5 stains and M=25 wavelength bins to choose, then there are 53,130 possible combinations. The analysis process involving Eq. [9] takes less than one minute using Matlab (MathWorks Inc., Natick, Mass.) running on a 450 MHz Pentium workstation. Each of the possible S matrices is examined under Eq. [9] to find the one matrix with the highest stability. In some instances a group matrices form an optimum group as opposed to a single optimum matrix. That is, there may be several matrices that make up a group, all of which exhibit comparable stability measures, and all of which are higher than the stability measures of the rest of the matrices. Mathematically, all these matrices are expected to produce comparable results in analyzing samples. Under such conditions, other exigencies such as hardware constraints may determine which matrix from within such an optimum group is chosen, or if there is no such constraint, one may choose freely from among the group.

The set of wavelength bins $\{\lambda_i\}$ that maximizes the stability of Eq. [9] is used to define matrix S. Having chosen the wavelength bins at which to measure the spectral response, the method chooses the intensities with which to measure the sample at each of the $\{\lambda_i\}$ wavelength bins (Step 14). These intensities form the matrix A.

Similar to the reasoning used above, the matrix A is chosen such that the stability of its inverse is optimized. The stability is determined using the same measure as in Eq. [7]. This stability measure is maximized when the square matrix A is a diagonal matrix, i.e. the best stability is obtained when one measures the sample with substantially the pure bands just derived.

This can be understood as follows. Off-diagonal components of A will reduce the det[A], while simultaneously increasing the denominator of Eq. [7]. These results reduce the stability of the inverse. The values of A are the intensities of each wavelength within each spectrum and the stability is optimized when each measurement spectrum has only one wavelength. Consecutive single wavelength bin measurements (that is, a succession of measurements in each of which only a single wavelength bin is used) is optimal for stability of the solution in the case using the minimum number of exposures required to obtain a solution. Having more than a single wavelength bin per measurement spectrum (off diagonal terms of A) will reduce the stability of the inverse, and exacerbate the effect of any small errors in A.

Having determined the optimum matrix A, the method obtains data from the sample (Step 16). The sample is measured with light whose spectral intensity at wavelength bin $\lambda_w$ is given by $A_{k,w}$ resulting in the intensity image $B_k$. Typically a spectral imaging system illuminates the sample and records the intensity images. In some embodiments, the intensity images are corrected for hardware errors such as dark current.

After collecting the N intensity images, the method uses Eqs. [6] and [8] and computes the stain concentrations (Step 18).

As mentioned above, some embodiments use K>W or W>N. In other words, for N stains the method may use more than N wavelength bins or the method may use more exposures than the number of wavelengths. In such embodiments, the method employs techniques such as a least square error approach to solve Eqs. [5] or [7] respectively. A suitable technique is Singular Value Decomposition (SVD), see, for example, William H. Press et al. in *Numerical Recipes in C: The art of scientific computing*, pp 59–70, Cambridge University Press, Cambridge 1999. In addition, nonsquare matrices will use measure of stability different than that Eq. [7]. A more general measure of stability suitable for both square and nonsquare matrices involves the Frobenius norm $\|X\|_F$ which for a matrix X is defined as:

$$\|X\|_F = \left(\sum_{i=1}^{n}\sum_{j=1}^{m}|x_{i,j}|^2\right)^{1/2}. \quad [11]$$

The stability is then given by the inverse of the conditional number c(X), which is defined as:

$$c(X) = \|X\|_F \|X^{-1}\|_F \quad [12].$$

Notably, the stability measure defined by Eqs. [11] and [12] reduce to the Schwarz measure of Eq. [9] for square 2×2 matrices. In general, such stability measures compute the dependence of the values of the inverse on small perturbations in the values of the matrix being inverted. Given the computations used to invert Eqs. [5] or [7], for example, such as those used in SVD, the method applies standard techniques for calculating error propagation to compute the resulting error in the stain concentrations. The method optimizes the matrices A and S so as to minimize the propagated error in the computed stain concentrations.

In some embodiments, the method is applied to optically thin samples; for example, the sample can be either physically thin or have a low concentration of absorbing stains. Some embodiments measure the fluorescence response of the samples, and typically the analysis given here is applicable to such embodiments. Under such conditions where $$\sum_{i=1}^{N} s_{j,i} c_i \ll 1,$$

the exponential of Eq. [4] can be linearized as follows $$B_k = \sum_{j=1}^{M} A_{k,j} \exp\left[-\sum_{i=1}^{N} s_{j,i} c_i\right] \quad [13]$$

$$\approx \sum_{j=1}^{M} A_{k,j} \left(1 - \sum_{i=1}^{N} s_{j,i} c_i\right)$$

$$= \sum_{j=1}^{M} A_{k,j} - \sum_{j=1}^{M} A_{k,j} \sum_{i=1}^{N} s_{j,i} c_i$$

$$= \sum_{j=1}^{M} A_{k,j} - \sum_{i=1}^{N} c_i \sum_{j=1}^{M} s_{j,i} A_{k,j}$$

Rearrangement of Eq. [13] yields $$\sum_{i=1}^{N} c_i \sum_{j=1}^{M} s_{j,i} A_{k,j} = \sum_{j=1}^{M} A_{k,j} - B_k \quad [14]$$

The right hand side of Eq. [14] is the total amount of light that is absorbed and not transmitted through to the detector. By virtue of the assumption in this special case, this value is very small. But with fluorescent epi-illumination, light which is absorbed can be emitted at a different wavelength in all directions. Hence a geometric fraction of the RHS of Eq. [14] will be detected if the microscope is in an epi-illumination mode. The fraction of energy detected is defined as $$D_k = g\left(\sum_{j=1}^{M} A_{k,j} - B_k\right) \quad [15]$$

where $g<1$ is the fraction of absorbed light re-emitted at a different wavelength which could be detected. In embodiments measuring light transmission with optically thin samples $g=1$. Eq. [14] is rewritten in matrix form by considering the K measurement spectra $$\begin{bmatrix} A_{1,1} & \cdots & A_{W,1} \\ \vdots & \ddots & \vdots \\ A_{1,K} & \cdots & A_{W,K} \end{bmatrix} \begin{bmatrix} s_{1,1} & \cdots & s_{N,1} \\ \vdots & \ddots & \vdots \\ s_{W,1} & \cdots & s_{W,N} \end{bmatrix} \cdot \begin{bmatrix} c_1 \\ \vdots \\ c_N \end{bmatrix} = \frac{1}{g} \begin{bmatrix} D_1 \\ \vdots \\ D_K \end{bmatrix} \quad [16]$$

The concentrations of the different stains are found by inverting Eq. [16]:

$$\begin{bmatrix} c_1 \\ \vdots \\ c_N \end{bmatrix} = \frac{1}{g} \begin{bmatrix} s_{1,1} & \cdots & s_{N,1} \\ \vdots & \ddots & \vdots \\ s_{W,1} & \cdots & s_{W,N} \end{bmatrix}^{-1} \begin{bmatrix} A_{1,1} & \cdots & A_{W,1} \\ \vdots & \ddots & \vdots \\ A_{1,K} & \cdots & A_{W,K} \end{bmatrix}^{-1} \cdot \begin{bmatrix} D_1 \\ \vdots \\ D_K \end{bmatrix} \quad [17]$$

The different wavelengths and their amplitudes of illumination are chosen to minimize the sensitivity to small errors as discussed in the general case. This can be accomplished by a judicious choice of the wavelength bins for measurement by the combinatorial method described above, and then utilizing consecutive single wavelength bin measurement. Note that a transform to optical density (by taking the natural logarithm) is not needed.

Figure 2:
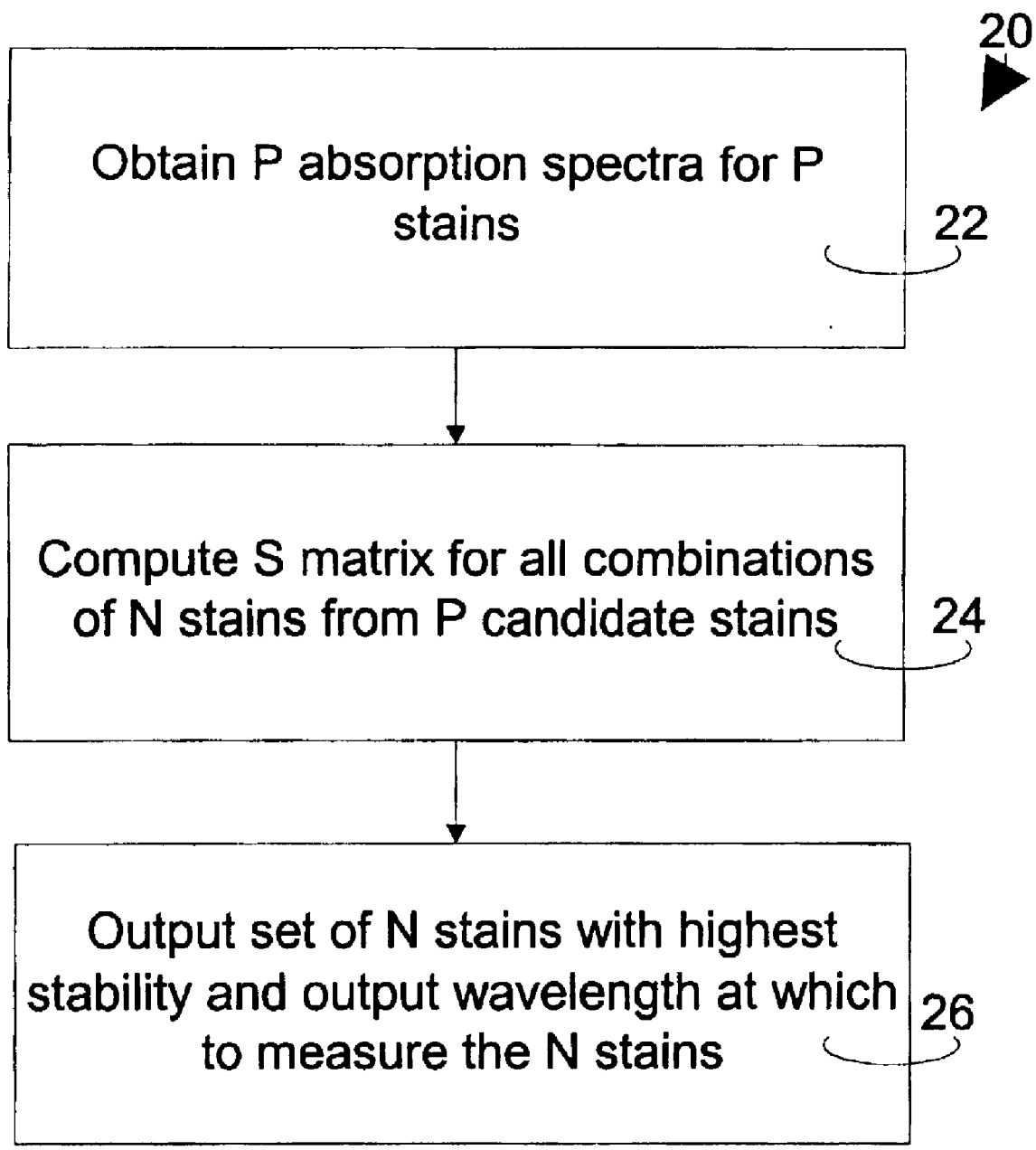
FIG. 2 is a flow diagram of a method for selecting N stains from among P candidate stains.

Method 10 as discussed above is applied to the analysis of a sample that has already been stained with N stains. In some cases, a researcher is free to choose N stains from among a group of P candidates. Referring to FIG. 2, a method 20 for choosing an optimum set of N stains from among P candidates is outlined. First the method obtains P absorption spectra for the P candidate stains. Similar techniques as described in method 10 are employed to obtain the absorption spectra in method 20 (Step 22). Having obtained the spectra, method 20 computes the optimum S (Step 24). The method first chooses a set of N stains from amongst the P candidates and using the N stains the method computes the possible S matrices. As above, the S matrix is the W×N matrix with elements $S_{ji}$, that are the absorption coefficients for the ith stain at the jth wavelength bin. From the group of P candidate stains, method 20 attempts all possible combinations of choosing N stains from the group of P candidates. Similar to the discussion above, method 20 then computes all the possible S matrices for each combination of N stains. For each possible S matrix, the method determines a stability for the inverse of the possible S matrix. The method determines the optimum choice of N stains from among the P candidates and the optimum W wavelengths bins at which to measure the spectral response for spectral unmixing of the N stains. Having chosen the optimum set of N stains, a researcher can apply the N protocols for applying each of the N stains to a sample and then the researcher applies method 10 to measure and compute the N stain concentrations.

In some embodiments, the choice of candidate stains includes choosing a stain from N groups of stains with $P_i$ candidates in each of the N groups. The method computes all possible S matrices and then chooses the matrix with the highest stability. The techniques for enumerating each of the possible combinations are well known from combinatorial theory. In yet other embodiments, other combinatorial constraints are used.

As described above, the spectral response of a sample is often measured using a spectral imaging apparatus. Typically a spectral imaging apparatus is capable of measuring the spectral response of a sample over a bandwidth Δ. In some embodiments, a spectral imaging apparatus is designed to be dedicated to analyzing samples that have been treated with a selected group of stains. Applying method 10 to such samples, the method computes the wavelength bins at which to measure the spectral response of the sample. In such embodiments, the spectral imaging system used to obtain the data from the samples (Step 16 of method 10) need not be capable of measuring the spectral response throughout the entire bandwidth Δ. The spectral apparatus measures the spectral response at the wavelength bins $\{\lambda_i\}$ chosen for the optimum matrix S. Because not all the wavelengths are needed for the measurements, typically such a spectral imaging apparatus is less expensive to build and often is smaller in size.

In some embodiments, the steps described above are implemented in computer programs using standard programming techniques. Such programs are designed to execute on programmable computers each comprising an electronic processor, a data storage system (including memory and/or storage elements), at least one input device, and least one output device, such as a display or printer. The program code is applied to control any of the following: the acquisition of the stain spectral responses, the computation of the S or A matrices, the acquisition of the sample data, the calculation of the stain concentrations, or the selecting a group of stains from a candidate group. The code is applied to the acquired data to perform the functions described herein and generate output information, which is applied to one or more output devices. Each such computer program can be implemented in a high-level procedural or object-oriented programming language, or an assembly or machine language. Furthermore, the language can be a compiled or interpreted language. Each such computer program can be stored on a computer readable storage medium (e.g., CD ROM or magnetic diskette) that when read by a computer can cause the processor in the computer to perform the analysis described herein.

A number of embodiments of the invention have been described. Nevertheless, it will be understood that various modifications may be made without departing from the spirit and scope of the invention. Accordingly, other embodiments are within the scope of the following claims.

What is claimed is:

1. A method comprising:
   measuring the intensity of a spectral response of at least one region of a sample stained with N multiple stains to each of K spectra $A_k$, (where k takes on integral values 1 and K) wherein the K spectra collectively include energy at W wavelength bins and where $K \geq N$; and
   determining the concentration of at least one of the stains in the region of the sample based in part on the spectral responses,
   wherein a matrix of elements that represent the response of each of the N stains at each of the W wavelength bins has an inverse for which a mathematical stability is maximum relative to the inverses of other matrices of elements that represent the responses of the stains for other possible sets of wavelength bins.

2. The method of claim 1 further comprising:
   determining the concentration of all of the multiple stains in the region of the sample based in part on the spectral responses.

3. The method of claim 1 wherein each of the spectra $A_k$ has energy at only one of the W wavelength bins.

4. The method of claim 1 wherein W=K.

5. The method of claim 1 wherein W=N.

6. The method of claim 1 wherein W=K=N.

7. The method of claim 1 wherein determining the concentration of the at least one stain comprises an optical density conversion.

8. The method of claim 5 wherein the mathematical stability of the inverse of the matrix of elements S is proportional to $$\frac{\det[S]}{\sum_{i=1}^{K}\sum_{j=1}^{W}(S_{i,j})^2}$$

where $S_{ij}$ is an element of S for $i^{th}$ stain at the $j^{th}$ wavelength bin.

9. The method of claim 1 wherein the spectral response of the sample comprises an absorption response.

10. The method of claim 1 wherein the spectral response of the sample comprises a fluorescence response.

11. The method of claim 1 wherein the sample comprises an optically thin sample.

12. The method of claim 1 wherein measuring the intensity of the spectral response for each spectra $A_k$ comprises: illuminating the region of the sample with radiation corresponding to each of the K spectra $A_k$, and measuring the intensity of radiation emerging from the region of the sample in response to the illumination with each spectra $A_k$.

13. The method of claim 1 wherein measuring the intensity of the spectral response for each spectra $A_k$ comprises: illuminating the region of the sample with broadband radiation, filtering the radiation emerging from the region of the sample in response to the broadband illumination with a filter corresponding to each of the K spectra $A_k$, and measuring the intensity of the filtered radiation for each of the K spectra $A_k$.

14. The method of claim 1 further comprising selecting the W wavelength bins based at least in part on the mathematical stability of the inverse of the matrix of elements that represent the response of each of the N stains at each of the W wavelength bins.

15. A method comprising:
   obtaining a spectral response for each of P stains; and
   selecting a set of W wavelength bins such that a matrix of elements that represent the responses of N of the P stains at the W wavelength bins has an inverse for which a mathematical stability is maximum relative to the inverses of other matrices of elements that represent the responses of the stains for other possible sets of wavelength bins and choices of N stains.

16. The method of claim 15 wherein P=N.

17. The method of claim 15 wherein P>N.

18. The method of claim 15 wherein W=N.

19. The method of claim 15 wherein the spectral response comprises absorption response.

20. The method of claim 15 wherein the spectral response comprises fluorescence response.

21. The method of claim 15 further comprising
   instructing a spectral imaging apparatus to measure the spectral response of a sample stained with the N stains to measure the spectral response at the set of wavelength bins.

22. The method of claim 18 wherein the mathematical stability of the inverse of the matrix of elements S is proportional to $$\frac{\det[S]}{\sum_{i=1}^{N}\sum_{j=1}^{W}(S_{i,j})^2}$$

where $S_{ij}$ is an element of S for $i^{th}$ stain at the $j^{th}$ wavelength bin.

23. A method comprising:
   obtaining a spectral response for each of P stains;
   determining, for each of multiple sets of W wavelength bins, the mathematical stability of an inverse of a matrix of elements that represent the responses of N of the P stains to the corresponding set of W wavelength bins; and
   selecting one of the multiple sets of W wavelength bins based at least in part on the magnitude of its mathematical stability relative to those of the other sets of wavelength bins.

24. The method of claim 23 wherein P=N.

25. The method of claim 23 wherein P>N.

26. The method of claim 23 wherein W=N.

27. The method of claim 23 further comprising measuring the intensity of a spectral response of at least one region of a sample stained with the N stains to each of K spectra $A_k$, (where k takes on integral values 1 and K) wherein the K spectra collectively include energy at the W wavelength bins and where K≧N; and determining the concentration of at least one of the stains in the region of the sample based in part on the spectral responses of the sample.

28. The method of claim 27 further comprising determining the concentration of all of the multiple stains in the region of the sample based in part on the spectral responses.

29. The method of claim 27 wherein each of the spectra $A_k$ has energy at only one of the W wavelength bins.

30. The method of claim 27 wherein W=K.

31. The method of claim 27 wherein W=K=N.

32. The method of claim 27 wherein determining the concentration of the at least one stain comprises an optical density conversion.

33. The method of claim 26 wherein the mathematical stability of the inverse of the matrix of elements S is proportional to $$\frac{\det[S]}{\sum_{i=1}^{N} \sum_{j=1}^{W} (S_{i,j})^2}$$

where $S_{ij}$ is an element of S for $i^{th}$ stain at the $j^{th}$ wavelength bin.

34. The method of claim 27 wherein the spectral response of the sample comprises an absorption response.

35. The method of claim 27 wherein the spectral response of the sample comprises a fluorescence response.

36. The method of claim 27 wherein the sample comprises an optically thin sample.

37. The method of claim 27 wherein measuring the intensity of the spectral response for each spectra $A_k$ comprises: illuminating the region of the sample with radiation corresponding to each of the K spectra $A_k$, and measuring the intensity of radiation emerging from the region of the sample in response to the illumination with each spectra $A_k$.

38. The method of claim 27 wherein measuring the intensity of the spectral response for each spectra $A_k$ comprises: illuminating the region of the sample with broadband radiation, filtering the radiation emerging from the region of the sample in response to the broadband illumination with a filter corresponding to each of the K spectra $A_k$, and measuring the intensity of the filtered radiation for each of the K spectra $A_k$.

39. A method comprising:

based on spectral responses of N stains at each of a set of M wavelength bins selecting W of the wavelength bins for measurement of a sample containing the N stains, the W wavelength bins being selected to minimize errors in stain concentration computed from the measurement of the sample where, N<W<M.

40. An apparatus comprising:

a spectral illuminator to emit light in W wavelength bins, with the intensity of light in each spectral band being independently adjustable, and a detector to measure a spectral response of a sample stained with N stains, wherein the W wavelength bins in the spectral illuminator are selected such that a matrix of elements that represent responses of the N stains at the W wavelength bins has an inverse for which a mathematical stability is maximum relative to the inverses of other matrices of elements that represent the responses of the N stains for other possible sets of wavelength bins.

41. The apparatus of claim 40 wherein W=N.

42. The apparatus of claim 40 wherein the spectral response of the sample comprises an absorption response.

43. The apparatus of claim 40 wherein the spectral response of the sample comprises a fluorescence response.

44. The apparatus of claim 41 wherein the mathematical stability of the inverse of the matrix of elements S is proportional to $$\frac{\det[S]}{\sum_{i=1}^{N} \sum_{j=1}^{W} (S_{i,j})^2}$$

where $S_{ij}$ is an element of S for $i^{th}$ stain at the $j^{th}$ wavelength bin.

* * * * *